(12) United States Patent
Talpade et al.

(10) Patent No.: US 7,194,297 B2
(45) Date of Patent: Mar. 20, 2007

(54) IMPEDANCE-MATCHING APPARATUS AND CONSTRUCTION FOR INTRAVASCULAR DEVICE

(75) Inventors: Dnyanesh Talpade, Plymouth, MN (US); Scott R. Smith, Chaska, MN (US); Kevin D. Edmunds, Circle Pines, MN (US); Kenneth R. Larson, Monticello, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 647 days.

(21) Appl. No.: 10/008,380

(22) Filed: Nov. 13, 2001

(65) Prior Publication Data

US 2003/0097064 A1 May 22, 2003

(51) Int. Cl.
*A61B 6/00* (2006.01)
(52) U.S. Cl. .............. 600/434; 600/407; 600/410; 600/464; 600/467; 600/470; 604/103; 324/300
(58) Field of Classification Search .......... 600/407, 600/410, 417, 423, 434, 464, 467, 470; 324/300–309; 604/93.01, 96.01, 101.01–102.02, 103.06, 604/103
See application file for complete search history.

(56) References Cited

U.S. PATENT DOCUMENTS

| 3,326,207 | A |   | 6/1967  | Egan |
| 4,304,239 | A |   | 12/1981 | Perlin ............... 128/642 |
| 4,740,752 | A |   | 4/1988  | Arakawa et al. ........ 324/318 |
| 4,899,757 | A |   | 2/1990  | Pope, Jr. et al. ....... 128/662.06 |
| 5,050,607 | A |   | 9/1991  | Bradley et al. .......... 128/653 |
| 5,109,859 | A | * | 5/1992  | Jenkins .................. 600/439 |
| 5,243,988 | A | * | 9/1993  | Sieben et al. ........... 600/463 |
| 5,269,319 | A | * | 12/1993 | Schulte et al. .......... 607/123 |
| 5,275,597 | A | * | 1/1994  | Higgins et al. .......... 606/33 |
| 5,318,025 | A |   | 6/1994  | Dumoulin et al. ....... 123/653.2 |
| 5,354,324 | A |   | 10/1994 | Gregory ................ 607/92 |
| 5,364,392 | A |   | 11/1994 | Warner et al. ........... 606/34 |
| 5,405,346 | A |   | 4/1995  | Grundy et al. .......... 606/41 |
| 5,438,997 | A | * | 8/1995  | Sieben et al. ........... 600/463 |
| 5,470,352 | A |   | 11/1995 | Rappaport .............. 607/101 |
| 5,476,095 | A |   | 12/1995 | Schnall et al. .......... 128/653.2 |
| 5,513,637 | A |   | 5/1996  | Twiss et al. ........... 128/653.01 |
| 5,543,712 | A |   | 8/1996  | Arakawa et al. ......... 324/318 |

(Continued)

FOREIGN PATENT DOCUMENTS

WO    WO 00/33734    6/2000

*Primary Examiner*—Brian L. Casler
*Assistant Examiner*—William Jung
(74) *Attorney, Agent, or Firm*—Fish & Richardson P.C.

(57) ABSTRACT

Intravascular device for matching impedances of portions of an intravascular circuit and limiting RF signal-induced heating of intravascular conductors. An intravascular device includes alternating conductive and dielectric layers and an electrically conductive coil in a configuration that effects an impedance-matching circuit. Another embodiment of an intravascular device has cylindrical inner and outer walls formed of an expandable, electrically conductive material, the inner and outer walls being separated by a compressible dielectric material. Varying the pressure in the lumen defined by the inner wall changes the spacing between the inner and outer walls, thereby changing the capacitance between the inner and outer wall. Another embodiment of an intravascular device includes one or more coaxial chokes for limiting heating caused by currents induced by RF signals. A conductive shield of the choke is formed of a conductive polymer to further reduce heating effects. Other embodiments include different transmission lines and antenna structures.

31 Claims, 7 Drawing Sheets

U.S. PATENT DOCUMENTS

| | | |
|---|---|---|
| 5,676,151 A | 10/1997 | Yock .................... 128/662.06 |
| 5,693,082 A | 12/1997 | Warner et al. .............. 607/156 |
| 5,713,363 A | 2/1998 | Seward et al. ......... 128/662.06 |
| 5,713,854 A | 2/1998 | Inderbitzen et al. .......... 604/53 |
| 5,728,079 A | 3/1998 | Weber et al. ................ 604/280 |
| 5,776,176 A | 7/1998 | Rudie ........................ 607/101 |
| 5,792,055 A | 8/1998 | McKinnon .................. 600/410 |
| 5,807,330 A | 9/1998 | Teitelbaum .................... 604/96 |
| 5,819,737 A | 10/1998 | Young et al. ............ 128/653.2 |
| 5,840,031 A | 11/1998 | Crowley ...................... 600/440 |
| 5,868,674 A | 2/1999 | Glowinski et al. .......... 600/410 |
| 5,928,145 A * | 7/1999 | Ocali et al. ................. 600/410 |
| 6,097,985 A | 8/2000 | Kasevich et al. ........... 607/102 |
| 6,159,225 A | 12/2000 | Makower .................... 606/155 |
| 6,165,127 A | 12/2000 | Crowley ..................... 600/463 |
| 6,263,229 B1 * | 7/2001 | Atalar et al. ................. 600/423 |
| 6,284,971 B1 | 9/2001 | Atalar et al. .................. 174/36 |
| 6,304,769 B1 | 10/2001 | Arenson et al. ............. 600/424 |
| 6,458,098 B1 | 10/2002 | Kanesaka .............. 604/101.05 |
| 6,560,475 B1 | 5/2003 | Viswanathan ............... 600/410 |
| 6,592,526 B1 | 7/2003 | Lenker ....................... 600/463 |
| 6,593,884 B1 | 7/2003 | Gilboa et al. ............... 342/448 |
| 6,606,513 B2 * | 8/2003 | Lardo et al. ................. 600/411 |
| 6,628,980 B2 | 9/2003 | Atalar et al. ................. 600/423 |
| 6,675,033 B1 * | 1/2004 | Lardo et al. ................. 600/410 |
| 6,699,241 B2 | 3/2004 | Rappaport et al. ............ 606/33 |
| 2003/0016186 A1 | 1/2003 | Watanabe et al. ........... 343/912 |

* cited by examiner

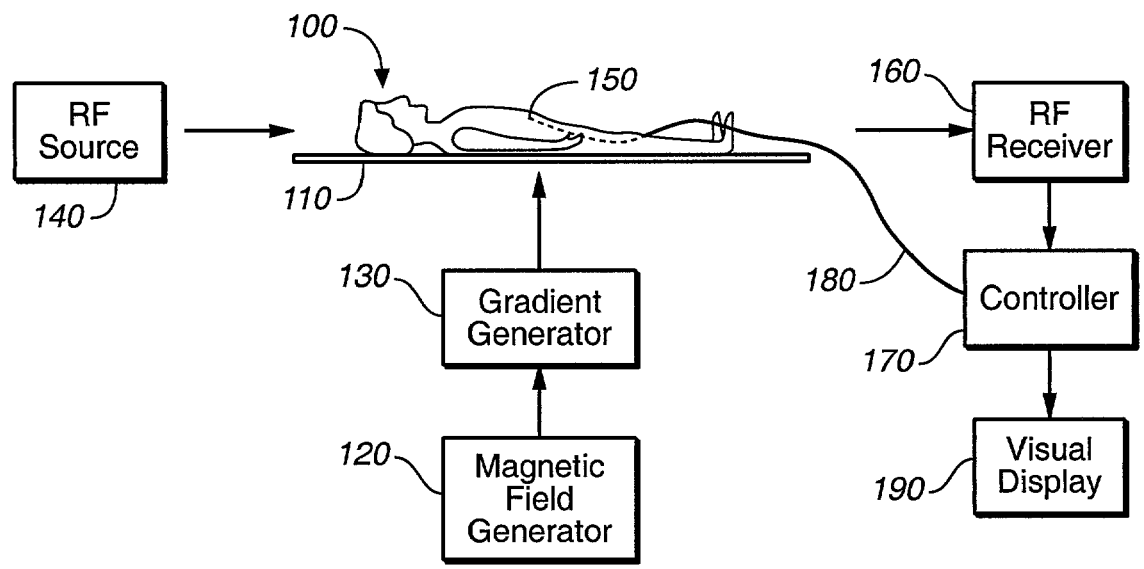
FIG._1
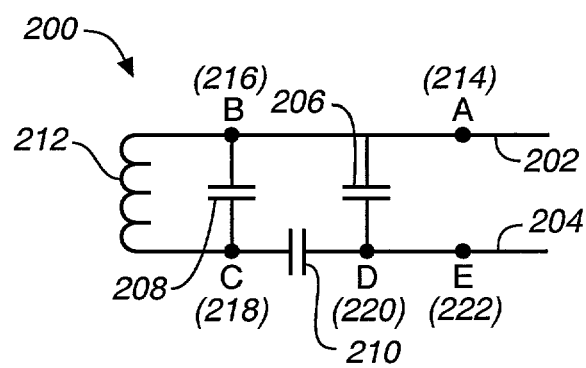
FIG._2
(PRIOR ART)

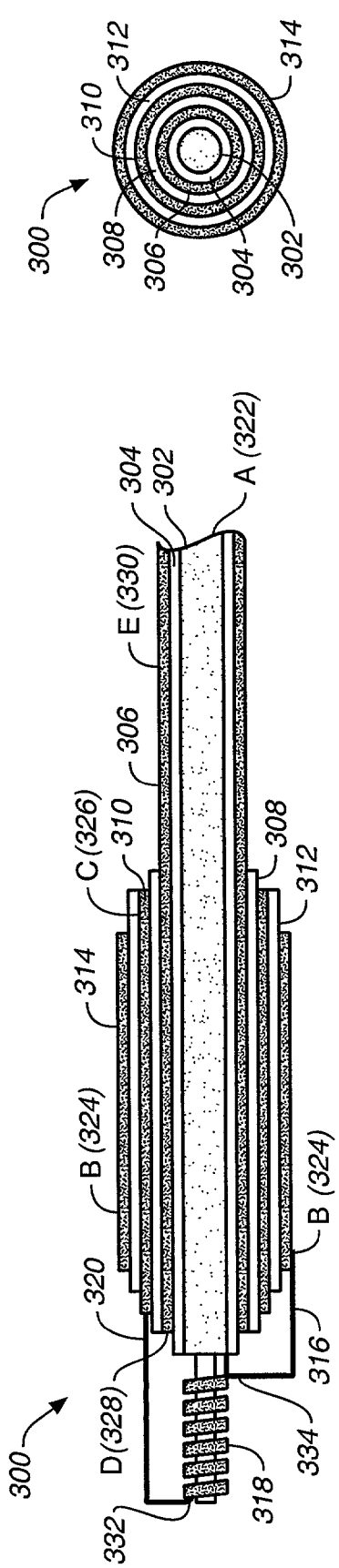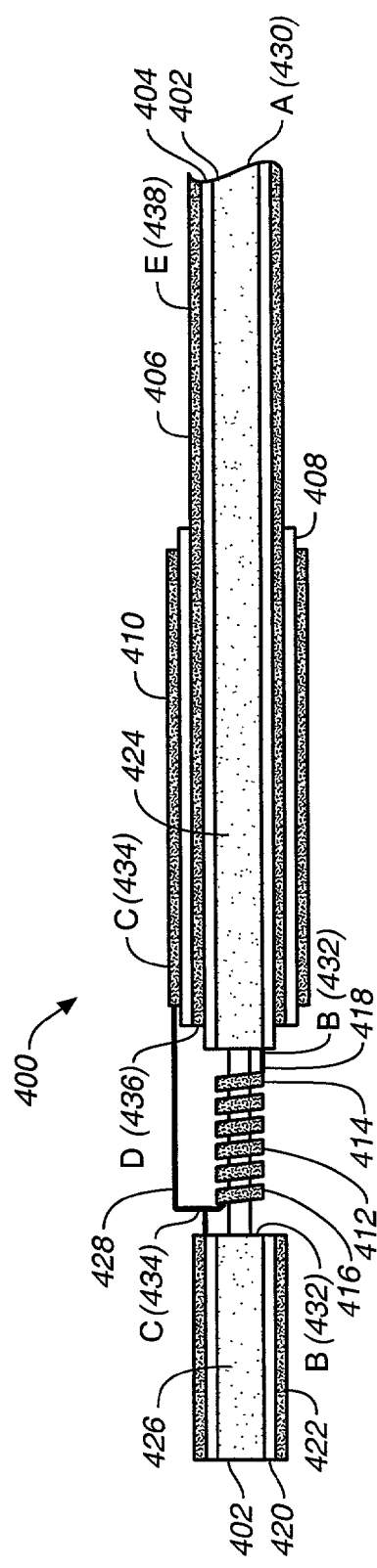

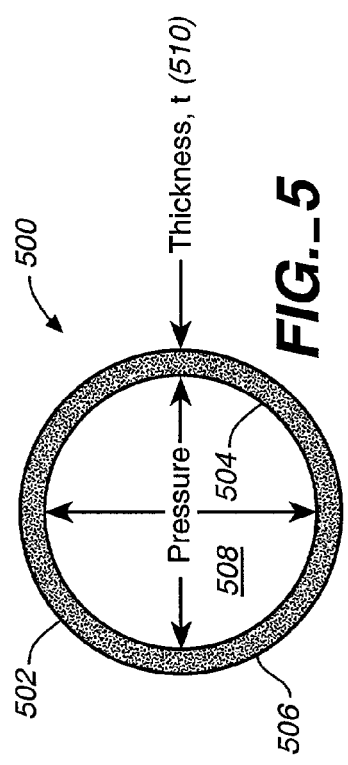
FIG._5
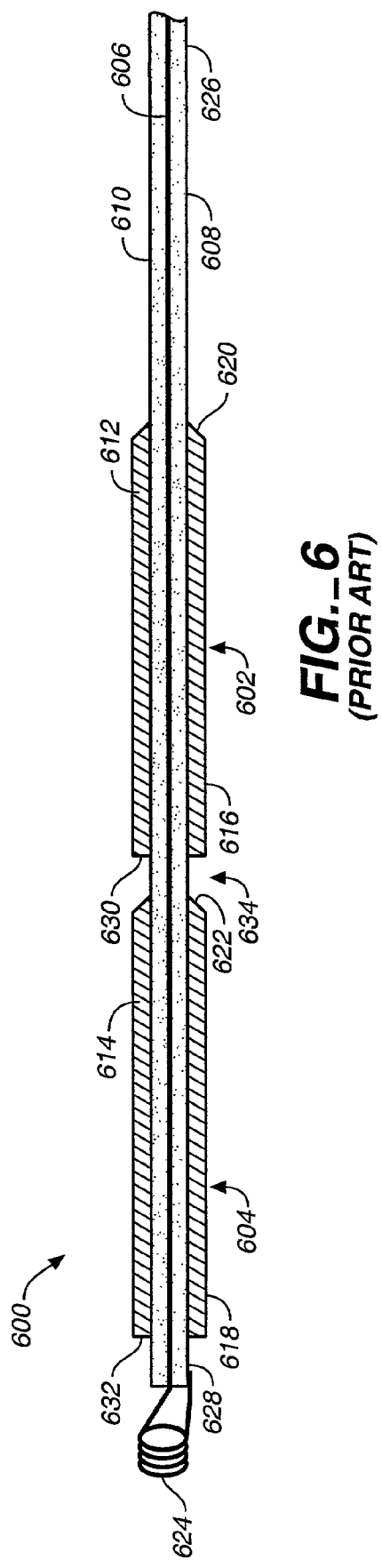
FIG._6
(PRIOR ART)

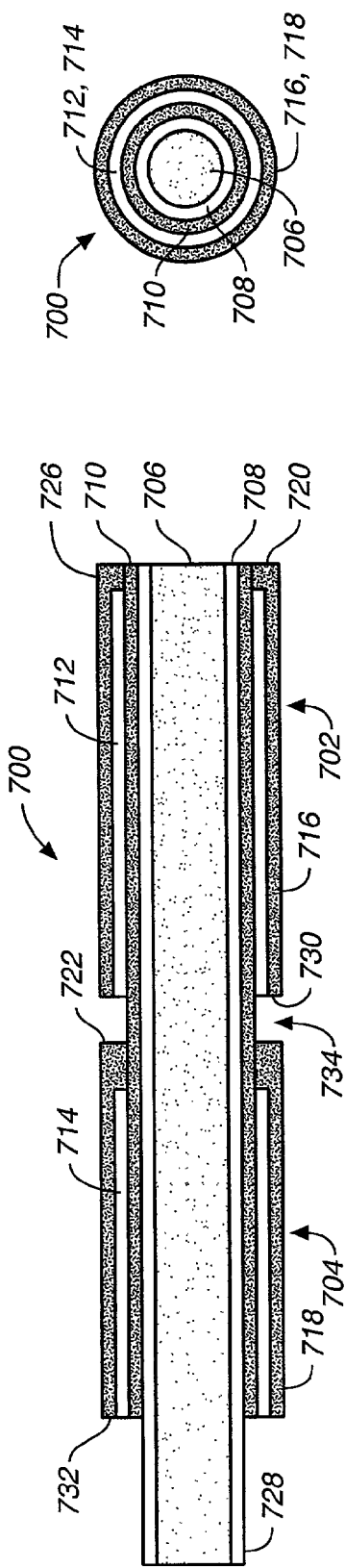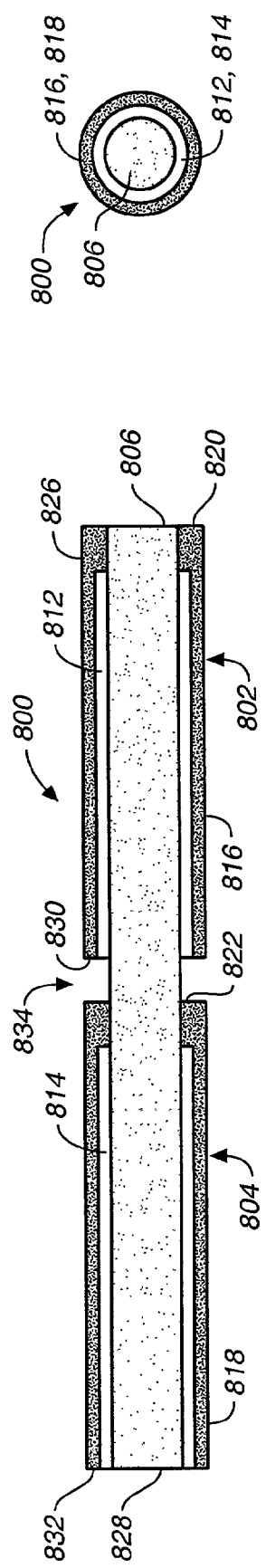

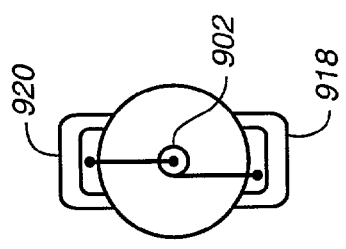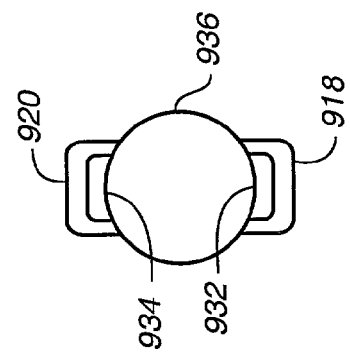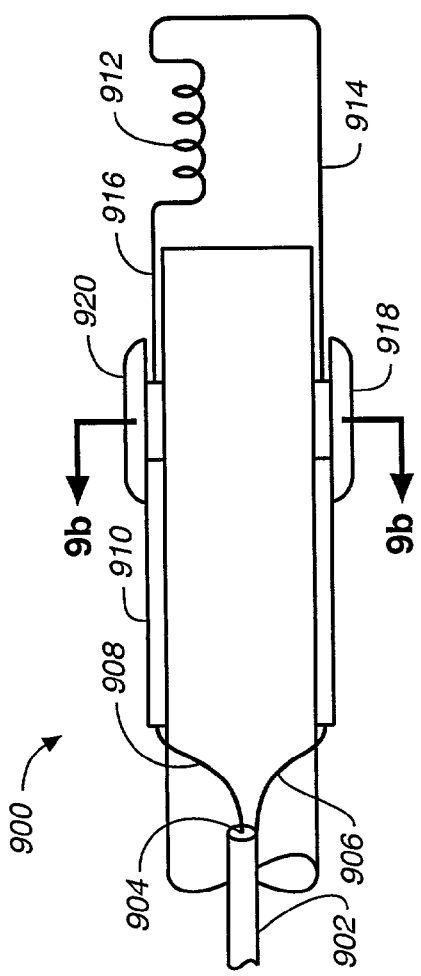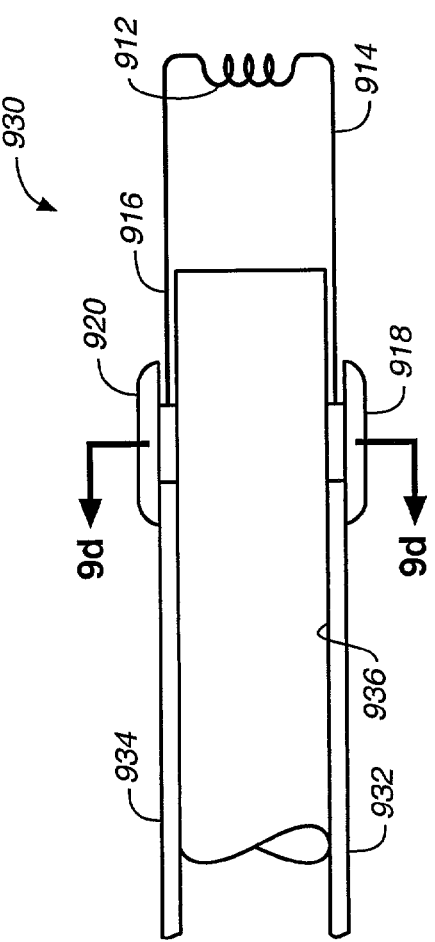

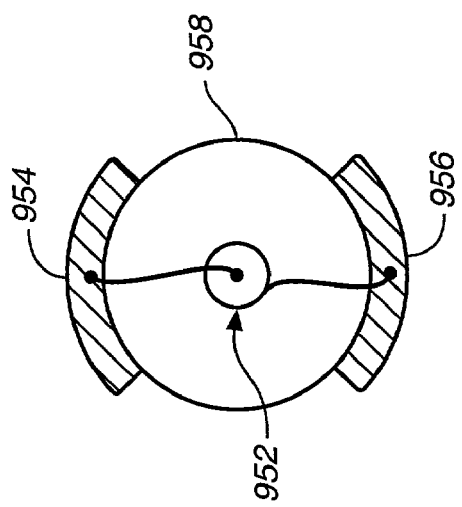
FIG._10b
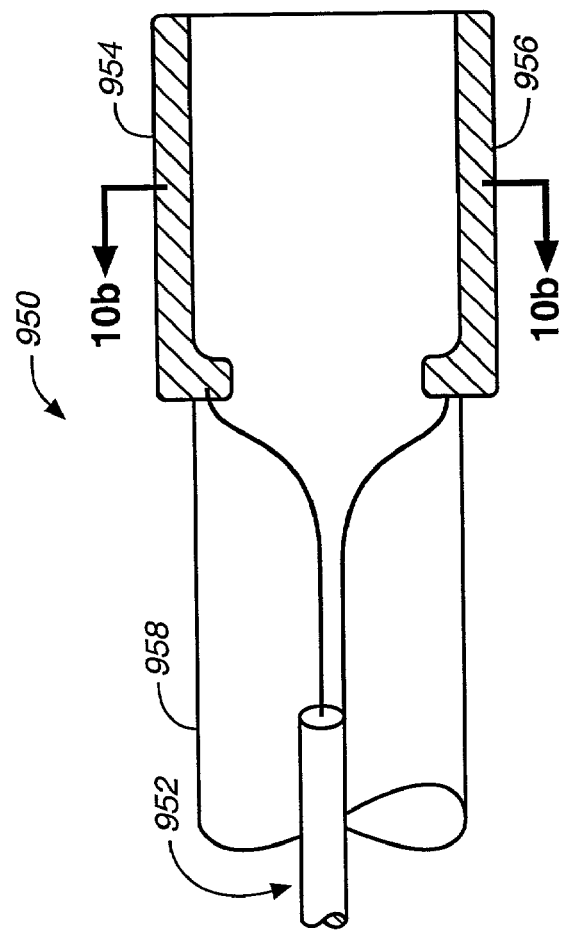
FIG._10a

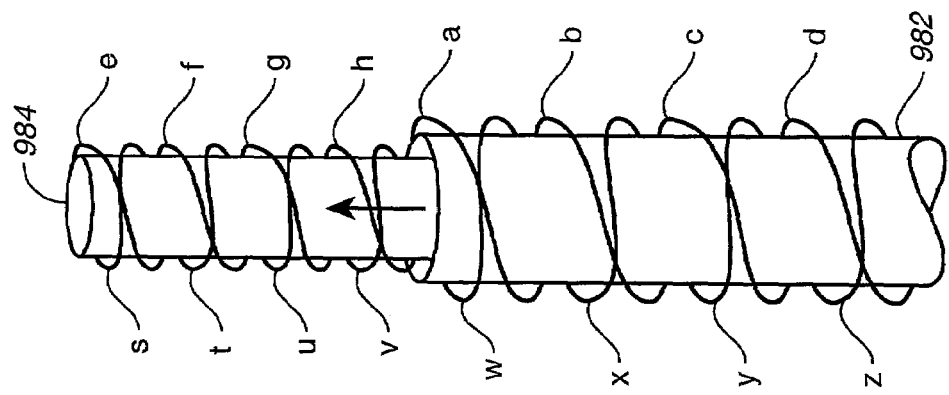
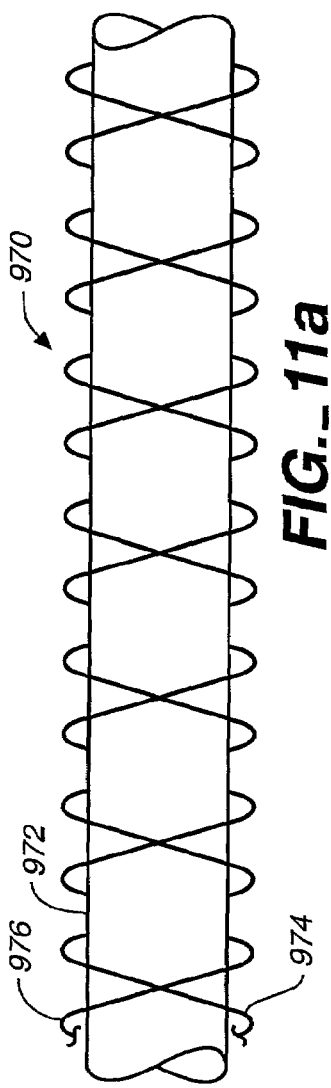
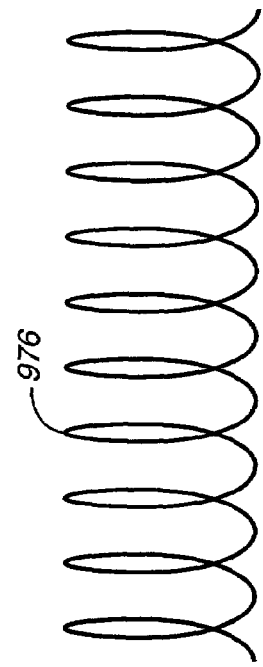
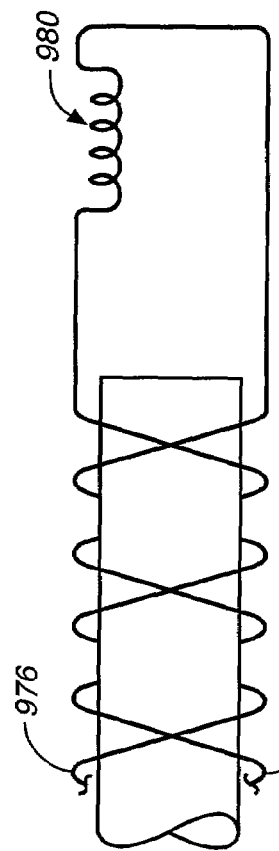

IMPEDANCE-MATCHING APPARATUS AND CONSTRUCTION FOR INTRAVASCULAR DEVICE

BACKGROUND OF THE INVENTION

The present invention relates generally to intravascular devices. More particularly, the present invention relates to impedance-matching among segments and construction of a transmission line associated with such an intravascular device.

Tracking of catheters and other devices positioned within a body may be achieved by means of a magnetic resonance imaging (MRI) system. Typically, such a magnetic resonance imaging system may be comprised of magnet, a pulsed magnetic field gradient generator, a transmitter for electromagnetic waves in radio frequency (RF), a radio frequency receiver, and a controller. In a common implementation, an antenna is disposed either on the device to be tracked or on a guidewire or catheter (commonly referred to as an MR catheter) used to assist in the delivery of the device to its destination. In one known implementation, the antenna comprises an electrically conductive coil that is coupled to a pair of elongated electrical conductors that are electrically insulated from each other and that together comprise a transmission line adapted to transmit the detected signal to the RF receiver.

In one embodiment, the coil is arranged in a solenoid configuration. The patient is placed into or proximate the magnet and the device is inserted into the patient. The magnetic resonance imaging system generates electromagnetic waves in radio frequency and magnetic field gradient pulses that are transmitted into the patient and that induce a resonant response signal from selected nuclear spins within the patient. This response signal induces current in the coil of electrically conductive wire attached to the device. The coil thus detects the nuclear spins in the vicinity of the coil. The transmission line transmits the detected response signal to the radio frequency receiver, which processes it and then stores it with the controller. This is repeated in three orthogonal directions. The gradients cause the frequency of the detected signal to be directly proportional to the position of the radio-frequency coil along each applied gradient.

The position of the radio frequency coil inside the patient may therefore be calculated by processing the data using Fourier transformations so that a positional picture of the coil is achieved. In one implementation this positional picture is superposed with a magnetic resonance image of the region of interest. This picture of the region may be taken and stored at the same time as the positional picture or at any earlier time.

In a coil-type antenna such as that described above, it is desirable that the impedance of the antenna coil substantially match the impedance of the transmission line. In traditional impedance matching of MRI coils, shunt-series or series shunt capacitor combinations suffice to tune the coil. In such traditional applications, the capacitors almost never pose a size constraint. However, for intravascular coils, miniaturization of the tuning capacitors is necessary. Discrete components have been employed to construct matching and tuning circuits on intravascular devices. But such components are bulky and are not easily incorporated into the design of the device. Also, placement of the tuning capacitors away from the coil without a reduction in the signal-to-noise ratio (SNR) is desirable. It has been proposed to use open circuit stub transmission lines as a means of fabricating arbitrary or trimmable capacitors and to use short-circuited stubs as tuning inductors. Such probes are tuned by trimming the length of the coaxial cables. However, these circuits still result in a relatively large device that is not ideal for intravascular navigation. Also, the circuits require many connections and the fabrication process is relatively complex.

Another problem that arises with intravascular MRI antennas and intravascular guidewires used in conjunction with an MRI system is that the electrical conductors tend to pick up the RF signals from the MRI system. This results in a higher voltage on the conductors and unwanted heating of the conductors. One prior art method of dealing with such undesirable heating of conductors with respect to an intravascular MRI antenna employs two coaxial chokes in series on a triaxial cable. Each choke is prepared by soldering a short between the primary and secondary shields of the triaxial cable at one end and removing the secondary shield at the other end. A dielectric layer between the primary and secondary shields acts as a waveguide that translates the short into a high impedance at the open end of the choke. This reduces the heating of the conductors. However, since the shields are made from metallic conductors, some heating of the conductors still occurs.

In addition, general construction difficulties also present problems. Simply connecting the antenna back to the transmission line conductors in such a small environment is quite difficult.

The present invention addresses at least one of these and other problems and offers advantages over the prior art.

SUMMARY OF THE INVENTION

The present invention relates to elongated intravascular devices adapted to be advanced through a vessel of a subject. The present invention provides one or more constructions of MR catheters that improve impedance matching and/or are easier to manufacture in a fast and reliable manner.

One embodiment of the present invention is directed to an elongated intravascular device that includes an elongated electrical conductor, a first electrically conductive layer, at least one dielectric layer, and an electrically conductive coil. The first electrically conductive layer is disposed coaxially to the elongated electrical conductor. The dielectric layer is disposed between the elongated electrical conductor and the first electrically conductive layer. The first end of the coil is electrically coupled to the elongated electrical conductor. The second end of the coil is electrically coupled to the first electrically conductive layer. A circuit made up of the elongated electrical conductor, the electrically conductive layer, the dielectric layer and the coil forms an impedance-matching circuit.

Another embodiment of the present invention is directed to an intravascular device that has a cylindrical inner wall and a cylindrical outer wall. The cylindrical inner wall defines a lumen and is formed of an expandable electrically conductive material. The cylindrical outer wall is also formed of an expandable electrically conductive material. The inner and outer walls are separated by a compressible dielectric material, wherein varying the pressure in the lumen changes the spacing between the inner and outer walls, thereby changing the capacitance between the inner and outer wall.

Another embodiment of the present invention is directed to an elongated intravascular device that includes an elongated electrical conductor, first and second dielectric layers, a primary shield layer, a secondary shield layer, first and second electrical shorts, and a non-electrically-conductive gap in the secondary shield layer. The first dielectric layer is disposed on top of the elongated electrical conductor. The primary shield layer is electrically conductive and is disposed on top of the first dielectric layer. The second dielectric layer is disposed on top of the primary shield layer. The secondary shield layer is comprised of an electrically conductive polymer or thin deposited metal and is disposed on top of the second dielectric layer. The first electrical short couples the primary shield layer to the secondary shield layer at a first longitudinal position along the elongated electrical conductor. The second electrical short couples the primary shield layer to the secondary shield layer at a second longitudinal position, distal of the first longitudinal position, along the elongated electrical conductor. The non-electrically-conductive gap is located in the shield layer at a longitudinal position just proximal of the second electrical short.

Another embodiment of the present invention is directed to an elongated intravascular device that includes an elongated electrical conductor, a dielectric layer, a shield layer, first and second electrical shorts, and a non-electrically-conductive gap in the shield layer. The dielectric layer is disposed on top of the elongated electrical conductor. The shield layer is comprised of an electrically conductive polymer disposed on top of the dielectric layer. The first electrical short couples the elongated electrical conductor to the shield layer at a first longitudinal position along the elongated electrical conductor. The second electrical short couples the elongated electrical conductor to the shield layer at a second longitudinal position, distal of the first longitudinal position, along the elongated electrical conductor. The non-electrically-conductive gap is located in the shield layer at a longitudinal position just proximal of the second electrical short.

In still other embodiments, MR catheters are constructed using conductive epoxy, electroplating techniques, and/or modified braid structures.

These and various other features as well as advantages which characterize the present invention will be apparent upon reading of the following detailed description and review of the associated drawings.

BRIEF DESCRIPTION OF THE DRAWINGS

FIG. 1 is a partial block diagram of an illustrative magnetic resonance imaging and intravascular guidance system in which embodiments of the present invention can be employed.

FIG. 2 is a schematic diagram of an impedance-matching circuit that is known in the art.

FIG. 3a is a schematic diagram showing a side cross-sectional view of an intravascular device having a multilayer impedance matching circuit according to an illustrative embodiment of the present invention.

FIG. 3b is a schematic diagram showing an end cross-sectional view of an intravascular device having a multilayer impedance matching circuit according to an illustrative embodiment of the present invention.

FIG. 4 is a schematic diagram showing a side cross-sectional view of an intravascular device having a multilayer impedance matching circuit according to an illustrative embodiment of the present invention.

FIG. 5 is a schematic diagram showing a cross-sectional view of an intravascular device having a pressure-variable capacitance according to an illustrative embodiment of the present invention.

FIG. 6 is a schematic diagram showing a side cross-sectional view of a prior art triaxial intravascular device having two coaxial chokes.

FIG. 7a is a schematic diagram showing a side cross-sectional view of a triaxial intravascular device having two coaxial chokes according to an illustrative embodiment of the present invention.

FIG. 7b is a schematic diagram showing an end cross-sectional view of a triaxial intravascular device having two coaxial chokes according to an illustrative embodiment of the present invention.

FIG. 8a is a schematic diagram showing a side cross-sectional view of a coaxial intravascular device having two coaxial chokes according to an illustrative embodiment of the present invention.

FIG. 8b is a schematic diagram showing an end cross-sectional view of an intravascular device having two coaxial chokes according to an illustrative embodiment of the present invention.

FIGS. 9a–9d show an intravascular device having an antenna connected to the transmission line using a conductive epoxy.

FIGS. 10a and 10b show an intravascular device having an antenna connected to the transmission line using an electroplated connection.

FIGS. 11a–11d show different embodiments of intravascular devices with an antenna formed of or connected to a transmission line by a conductive braid.

DETAILED DESCRIPTION OF ILLUSTRATIVE EMBODIMENTS

FIG. 1 is a partial block diagram of an illustrative magnetic resonance imaging and intravascular guidance system in which embodiments of the present invention could be employed. In FIG. 1, subject 100 on support table 110 is placed in a homogeneous magnetic field generated by magnetic field generator 120. Magnetic field generator 120 typically comprises a cylindrical magnet adapted to receive subject 100. Magnetic field gradient generator 130 creates magnetic field gradients of predetermined strength in three mutually orthogonal directions at predetermined times. Magnetic field gradient generator 130 is illustratively comprised of a set of cylindrical coils concentrically positioned within magnetic field generator 120. A region of subject 100 into which a device 150, shown as a catheter, is inserted, is located in the approximate center of the bore of magnet 120.

RF source 140 radiates pulsed radio frequency energy into subject 100 and the MR active sample within device 150 at predetermined times and with sufficient power at a predetermined frequency to nutate nuclear magnetic spins in a fashion well known to those skilled in the art. The nutation of the spins causes them to resonate at the Larmor frequency. The Larmor frequency for each spin is directly proportional to the strength of the magnetic field experienced by the spin. This field strength is the sum of the static magnetic field generated by magnetic field generator 120 and the local field generated by magnetic field gradient generator 130. In an illustrative embodiment, RF source 140 is a cylindrical external coil that surrounds the region of interest of subject 100. Such an external coil can have a diameter sufficient to encompass the entire subject 100. Other geometries, such as smaller cylinders specifically designed for imaging the head or an extremity can be used instead. Non-cylindrical external coils such as surface coils may alternatively be used.

Device 150 is inserted into subject 100 by an operator. Device 150 may be a guide wire, a catheter, an ablation device or a similar recanalization device. Device 150 includes an RF antenna which detects MR signals generated in both the subject and the device 150 itself in response to the radio frequency field created by RF source 140. Since the internal device antenna is small, the region of sensitivity is also small. Consequently, the detected signals have Larmor frequencies which arise only from the strength of the magnetic field in the proximate vicinity of the antenna. The signals detected by the device antenna are sent to imaging and tracking controller unit 170 via conductor 180.

External RF receiver 160 also detects RF signals emitted by the subject in response to the radio frequency field created by RF source 140. In an illustrative embodiment, external RF receiver 160 is a cylindrical external coil that surrounds the region of interest of subject 100. Such an external coil can have a diameter sufficient to encompass the entire subject 100. Other geometries, such as smaller cylinders specifically designed for imaging the head or an extremity can be used instead. Non-cylindrical external coils, such as surface coils, may alternatively be used. External RF receiver 160 can share some or all of its structure with RF source 140 or can have a structure entirely independent of RF source 140. The region of sensitivity of RF receiver 160 is larger than that of the device antenna and can encompass the entire subject 100 or a specific region of subject 100. However, the resolution which can be obtained from external RF receiver 160 is less than that which can be achieved with the device antenna. The RF signals detected by external RF receiver 160 are sent to imaging and tracking controller unit 170 where they are analyzed together with the RF signals detected by the device antenna.

The position of device 150 is determined in imaging and tracking controller unit 170 and is displayed on display means 180. In an illustrative embodiment of the invention, the position of device 150 is displayed on display means 180 by superposition of a graphic symbol on a conventional MR image obtained by external RF receiver 160. Alternatively, images may be acquired with external RF receiver 160 prior to initiating tracking and a symbol representing the location of the tracked device be superimposed on the previously acquired image. Alternative embodiments of the invention display the position of the device numerically or as a graphic symbol without reference to a diagnostic image.

In an intravascular antenna such as that described above with respect to device 150, it is desirable that the impedance of the antenna coil substantially match the impedance of the transmission line. In traditional impedance matching of MRI coils, shunt-series or series shunt capacitor combinations suffice to tune the coil. In such traditional applications, the capacitors almost never pose a size constraint. However, for intravascular coils, miniaturization of the tuning capacitors is necessary. Discrete components have been employed to construct matching and tuning circuits on intravascular devices. But such components are bulky and are not easily incorporated into the design of the device. Also, it is desirable to maintain the signal-to-noise ratio (SNR). It has been proposed to use open circuit stub transmission lines as a means of fabricating arbitrary or trimmable capacitors and to use short-circuited stubs as tuning inductors. Such probes are tuned by trimming the length of the coaxial cables. However, these circuits still result in a relatively large device that is not ideal for intravascular navigation. Also, the circuits require many connections and the fabrication process is relatively complex.

To address the above-described problem, an illustrative embodiment of the present invention employs alternating layers of conductors and dielectric materials to construct components and circuits that can be used to tune a circuit of the intravascular device or to match impedances among components or segments of such a circuit. FIG. 2 is a schematic diagram of an impedance-matching circuit 200 that is known in the art. Impedance-matching circuit 200 includes transmission lines 202,204, capacitances 206, 208, 210, and inductive coil 212. For purposes of description, impedance-matching circuit 200 is shown having reference nodes A (214), B (216), C (218), D (220) and E (222).

FIG. 3a is a side cross-sectional view of an intravascular device 300 according to an illustrative embodiment of the present invention. FIG. 3b is an end cross-sectional view of intravascular device 300. Intravascular device 300 realizes impedance-matching circuit 200 by utilizing alternating layers of conductors and dielectric materials. In an illustrative embodiment of the present invention, intravascular device 300 is a device whose primary purpose is to function as an antenna, that is, to receive RF signals and transmit the signals back to a receiver/controller. In an alternative embodiment, intravascular device 300 performs functions in addition to its antenna functions. For example, in one embodiment, intravascular device 300 can also serve as a guidewire used to assist in the delivery of another intravascular device to an intravascular location. In another illustrative embodiment, intravascular device 300 can also serve as an ablation device used to disintegrate an occlusion in a vessel. In an illustrative embodiment, intravascular device 300 is deployed using a catheter. In a further embodiment, intravascular device 300 is integral with a catheter and disposed within the catheter shaft.

In FIGS. 3a and 3b, electrically conductive elements are indicated with dark shading and dielectric elements are shown without shading. Intravascular device 300 is an elongated coaxial device having a center conductor 302. Dielectric layer 304 separates center conductor 302 from electrically conductive shield layer 306. Dielectric layer 308 separates shield layer 306 from electrically conductive layer 310. Dielectric layer 312 separates electrically conductive layer 310 from electrically conductive layer 314. Center conductor 302 is electrically coupled to conductive layer 314 via connector 316. Connector 316 also electrically couples center conductor 302 to a first end 334 of electrically conductive coil 318. Coil 318 is illustratively adapted to receive RF signals and to transmit the signals to center conductor 302. Conductive layer 310 is electrically coupled to a second end 332 of electrically conductive coil 318 via connector 320. In the illustrative embodiment depicted in FIG. 3a, coil 318 is wound around a dielectric element extending from the distal end of center conductor 302. However, in accordance with the present invention, coil 318 can be positioned and configured in other arrangements. For example, in one embodiment, coil 318 is wound around center conductor 302 and dielectric layer 304, which, in such an embodiment, extends distally beyond shield layer 306, dielectric layers 308, 312 and conductive layers 310, 314.

The arrangement of conductive and dielectric layers of device 300 forms an impedance matching circuit that is equivalent to that shown in FIG. 2. Elements A (322), B (324), C (326), D (328) and E (330) in FIG. 3a correspond to nodes A (214), B (216), C (218), D (220) and E (222) of impedance-matching circuit 200 in FIG. 2. Element A (322) corresponds to center conductor 302. Element B (324) corresponds to conductive layer 314, which is electrically coupled to center conductor 302 and to the first end 334 of coil 318. Coil 318 corresponds to inductive coil 212 in FIG. 2. Thus, the second end 332 of coil 318 electrically couples to element C (326), which corresponds to conductive layer 310. Conductive elements B (324) and C (326) are separated by dielectric layer 312, which gives rise to a capacitance that corresponds to capacitance 208 in FIG. 2. Element D (328) corresponds to the distal end of shield layer 306. Element E (330) corresponds to the proximal end of shield layer 306. Conductive elements C (326) and D (328) are separated by dielectric layer 308, which gives rise to a capacitance that corresponds to capacitance 210 in FIG. 2. Conductive elements D (328) and A (322) are separated by dielectric layer 304, which gives rise to a capacitance that corresponds to capacitance 206 in FIG. 2. Thus, intravascular device 300 effects an impedance-matching circuit that functions substantially similarly to impedance-matching circuit 200 in FIG. 2.

FIG. 4 is a side cross-sectional view of an intravascular device 400 according to another illustrative embodiment of the present invention. Like device 300 in FIGS. 3a and 3b, intravascular device 400 realizes the impedance-matching circuit 200 of FIG. 2 by utilizing alternating layers of conductors and dielectric materials. In an illustrative embodiment of the present invention, intravascular device 400 is a device whose primary purpose is to function as an antenna, that is, to receive RF signals and transmit the signals back to a receiver/controller. In an alternative embodiment, intravascular device 400 performs functions in addition to its antenna functions. For example, in one embodiment, intravascular device 400 can also serve as a guidewire used to assist in the delivery of another intravascular device to an intravascular location. In another illustrative embodiment, intravascular device 400 can also serve as an ablation device used to disintegrate an occlusion in a vessel. In an illustrative embodiment, intravascular device 400 is deployed using a catheter. In a further embodiment, intravascular device 400 is integral with a catheter and disposed within the catheter shaft.

In FIG. 4, electrically conductive elements are indicated with dark shading and dielectric elements are shown without shading. Intravascular device 400 is an elongated coaxial device having a center conductor 402. Dielectric layer 404 separates electrically conductive shield layer 406 from longitudinal segment 424 of center conductor 402. Dielectric layer 408 separates shield layer 406 from electrically conductive layer 410. Center conductor 402 is electrically coupled to a first end 414 of electrically conductive coil 412 via connector 418. Coil 412 is illustratively adapted to receive RF signals and to transmit the signals to center conductor 402. Dielectric layer 420 separates electrically conductive shield layer 422 from longitudinal segment 426 of center conductor 402. A second end 416 of coil 412 is electrically coupled to both shield layer 422 and electrically conductive layer 410 via connector 428. In the illustrative embodiment depicted in FIG. 4, coil 412 is wound around a longitudinal segment of center conductor 402 that is between longitudinal portion 424 and longitudinal portion 426. However, in accordance with the present invention, coil 412 can be positioned and configured in other arrangements. For example, in one embodiment, coil 412 is wound independently of center conductor 402, rather than being wound around center conductor 402 as shown in FIG. 4. In another embodiment, coil 412 is wound around center conductor 402 at a longitudinal position that is either distal or proximal to both longitudinal portion 424 and longitudinal portion 426, as opposed to being positioned between longitudinal segments 424 and 426.

The arrangement of conductive and dielectric layers of device 400 forms an impedance matching circuit that is equivalent to that shown in FIG. 2. Elements A (430), B (432), C (434), D (436) and E (438) in FIG. 4 correspond to nodes A (214), B (216), C (218), D (220) and E (222) of impedance-matching circuit 200 in FIG. 2. Element A (430) corresponds to center conductor 402. Element B (432) corresponds to connector 418, which is electrically coupled to center conductor 402 and to the first end 414 of coil 412. Coil 412 corresponds to inductive coil 212 in FIG. 2. Thus, the first end 412 of coil 412 electrically couples to element C (434), which corresponds to connector 428, and which is electrically coupled to shield layer 422 and to conductive layer 410. Longitudinal section 426 of center conductor 402 (element B (432)) and conductive shield layer 422 (element C (434)) are separated by dielectric layer 420, which gives rise to a capacitance that corresponds to capacitance 208 in FIG. 2. Element D (436) corresponds to the distal end of shield layer 406. Element E (438) corresponds to the proximal end of shield layer 406. Conductive elements C (434) and D (436) are separated by dielectric layer 408, which gives rise to a capacitance that corresponds to capacitance 210 in FIG. 2. Conductive elements D (436) and A (430) are separated by dielectric layer 404, which gives rise to a capacitance that corresponds to capacitance 206 in FIG. 2. Thus, intravascular device 400 effects an impedance-matching circuit that functions substantially similarly to impedance-matching circuit 200 in FIG. 2.

FIG. 5 is a cross-sectional view of an elongated intravascular device 500 according to another embodiment of the present invention. Device 500 is a double-walled pressure vessel. Inner wall 504 is formed of an expandable electrically conductive material. Outer wall 502 is formed of an electrically conductive material. In an illustrative embodiment of the present invention, outer wall 502 is formed of a substantially rigid, non-expandable material. In an alternative embodiment, outer wall 502 is formed of an expandable material, similarly to inner wall 504. Inner wall 504 defines lumen 508. Outer wall 502 and inner wall 504 are separated by a compressible dielectric material 506 having a thickness, t 510. Because outer wall 502 and inner wall 504 are parallel conductive surfaces separated by a dielectric 506, a capacitance exists between outer wall 502 and inner wall 504.

In operation, varying the pressure in lumen 508 changes the spacing between outer wall 502 and inner wall 504. Varying the spacing in this way results in varying the capacitance between outer wall 502 and inner wall 504. The capacitance varies according to the formula:

$$C = \frac{2\pi\varepsilon L}{\ln(B/A)}$$

where $\varepsilon_0$ is the permittivity of dielectric 506, L is the length of the parallel conductive outer wall 502 and inner wall 504, A is the inner diameter (the diameter of inner wall 504) and B is the outer diameter (the diameter of outer wall 502). Varying the capacitance between inner wall 504 and outer wall 502 allows a circuit that includes conductive outer wall 502 and conductive inner wall 504 to be tuned. Such tuning may be desirable, for example, to compensate for the effect of the tissue surrounding intravascular device 500.

In an illustrative embodiment of intravascular device 500, outer wall 502 and inner wall 504 are part of a circuit that includes an electrically conductive coil. One end of the coil is electrically coupled to a distal end of outer wall 502 and the other end of the coil is electrically coupled to the distal end of inner wall 504. The proximal ends of outer wall 502 and inner wall 504 are illustratively coupled to transmission lines that are coupled to a receiver/controller. Such a circuit can be used as an antenna in an MRI system to detect RF signals and to transmit then to the receiver/controller. Varying the capacitance of outer wall 502 and inner wall 504 enables a matching of the impedances of the transmission lines to that of the coil and allows the antenna circuit to be tuned.

In an illustrative embodiment of intravascular device 500, the dielectric 506 is air. In an alternative embodiment, the dielectric material 506 is a porous, air-filled material. In one embodiment, expanded polytetraflouroethylene (PTFE), or EPTFE, or a material with similar structure and properties, is used as the dielectric 506. Expanded PTFE is a porous material that has a very low density. A dielectric made of expanded PTFE will consist mostly of air. Thus such a material can be easily compressed by hydrostatic pressure within the lumen 508 of device 500. This results in a larger variance in the thickness of the dielectric material and thus the capacitance is more readily manipulated.

As explained previously, in one embodiment of intravascular device 500, inner wall 504 is made of an expandable material while outer wall 502 is made of a substantially rigid material. In an alternative embodiment, both the inner wall 504 and outer wall 502 are made of an expandable material. In one embodiment, device 500 is formed of an expandable dielectric material that is coated with a conductive coating, such as a metal coating. In one embodiment, device 500 is formed by coating a balloon with a conductive coating.

In one embodiment of the present invention, intravascular device 500 is a catheter adapted to assist in the delivery of a substance or another intravascular device to an intravascular location. In another embodiment, intravascular device 500 is a balloon that can be inflated to prop open a vessel.

FIG. 6 is a schematic diagram of an intravascular device 600 that is known in the prior art. Intravascular device 600 is a triaxial cable having two choke mechanisms 602 and 604. Device 600 also includes center conductor 606, dielectric layer 608, primary shield 610 and electrically conductive coil 624. Choke 602 includes dielectric layer 612, secondary shield 616 and electrical short 620. Choke 604 includes dielectric layer 614, secondary shield 618 and electrical short 622. Primary shield 610 and secondary shields 616 and 618 are electrically conductive. Device 600 is commonly referred to in the art as a "bazooka bal-un."

The proximal end 626 of center conductor 606 extends to and couples to a receiver/controller (not shown). Dielectric layer 608 insulates primary shield 610 from center conductor 606. Dielectric layer 612 insulates secondary shield 616 from primary shield 610. Dielectric layer 614 insulates secondary shield 618 from primary shield 610. The distal end 628 of center conductor 606 is electrically coupled to one end of coil 624. The other end of coil 624 is electrically coupled to the distal end 628 of primary shield 610. Coil 624 serves as an antenna that can be employed in an MRI system to detect RF signals and to transmit them to a receiver/controller via center conductor 606 and primary shield 610. The RF pulses generated by the MRI system tend to induce currents in center conductor 606 and primary shield 610. Such induced currents cause high voltage to develop at impedance discontinuities. This creates strong electrical fields to develop in the surrounding tissue, and consequently, to undesirably heat any surrounding tissue. Furthermore, in an embodiment wherein intravascular device 600 serves as an ablation device, currents induced in center conductor 606 can cause the ablation tip to heat up at unintended junctures or can cause the ablation tip to heat up more than desired during ablation.

Coaxial chokes 602 and 604 serve to limit the induced currents in center conductor 606 and primary shield 610. Electrical short 620 couples secondary shield 616 to primary shield 610 at a proximal end of choke 602. Secondary shield 616 terminates at a distal end 630 of choke 602 without electrically coupling to either primary shield 610 or secondary shield 618. Thus, a gap 634 is formed between secondary shield 616 and secondary shield 618. Electrical short 622 couples secondary shield 618 to primary shield 610 at a proximal end of choke 604. Secondary shield 618 terminates at a distal end 632 of choke 604 capacitively coupling to primary shield 610. In an illustrative embodiment, shorts 620 and 622 are formed by soldering the secondary shields 616 and 618 to the primary shield 610.

The dielectric space 612 between primary shield 610 and secondary shield 616 acts as a waveguide that translates short 620 into a high impedance at the open end 630 of choke 602. Similarly, the dielectric space 614 between primary shield 610 and secondary shield 618 acts as a waveguide that translates short 622 into a high impedance at the open end 632 of choke 604. In an illustrative embodiment, the length of each choke 602, 604 (and thus the length of dielectric layers 612, 614 and secondary shields 616, 618) is one-fourth the wavelength of the electromagnetic radiation to be impeded. Thus, in a typical MRI system that employs RF radiation having a wavelength of 300 centimeters (cm), chokes 602 and 604 are designed to have a length of 75 cm. In an illustrative embodiment, the distance between the distal end 630 of choke 602 and short 622 of choke 604 is approximately 1.0 cm. Likewise, the distance between the distal end 632 of choke 604 and coil 624 is illustratively approximately 1.0 cm.

According to an illustrative embodiment of the present invention, a conductive polymer is employed to implement one or more shield layers in a bazooka bal-un device, such as secondary shield layers 616 and 618 of device 600. Conductive polymers generally have a higher resistivity than metal conductors. Therefore, lower amounts of current will be induced in a device employing conductive polymers than a device employing metal conductors, but must be conductive enough to effectively shield.

FIGS. 7a and 7b are schematic diagrams of an intravascular device 700 according to an illustrative embodiment of the present invention. FIG. 7a is a side cross-sectional view of device 700. FIG. 7b is an end cross-sectional view of device 700. Device 700 is somewhat similar to device 600 in FIG. 6. However, one substantial difference between device 600 and device 700 is that device 700 makes use of conductive polymers for the secondary shield layer, as is described below.

Intravascular device 700 is a triaxial device having two choke mechanisms 702 and 704. Device 700 also includes center conductor 706, dielectric layer 708 and primary shield 710. Choke 702 includes dielectric layer 712, secondary shield 716 and electrical short 720. Choke 704 includes dielectric layer 714, secondary shield 718 and electrical short 722. Primary shield 710 and secondary shields 716 and 718 are electrically conductive.

The proximal end 726 of center conductor 706 extends to and couples to a receiver/controller (not shown). Dielectric layer 708 insulates primary shield 710 from center conductor 706. Dielectric layer 712 insulates secondary shield 716 from primary shield 710. Dielectric layer 714 insulates secondary shield 718 from primary shield 710. Secondary shields 716 and 718 are formed of a conductive polymer in order to reduce the currents induced by RF radiation. In an illustrative embodiment, device 700 serves an antenna that can be employed in an MRI system to detect RF signals and to transmit them to a receiver/controller via center conductor 706 and primary shield 610. In an illustrative embodiment, the distal end 728 of center conductor 706 and the distal end of shield layer 710 are electrically coupled to opposite ends of an electrically conductive coil, in a manner similar to coil 624 of FIG. 6. In an illustrative embodiment, such a coil is wound around the distal end 728 of center conductor 706 and dielectric layer 708. In an alternative embodiment, device 700 is a monopole antenna or a coaxial antenna. In a monopole or coaxial antenna configuration, the distal end 728 of center conductor 706 and the distal end of shield layer 710 are electrically coupled to one another and the antenna picks up RF signals as a result of currents being induced in center conductor 706 and shield layer 710.

In an illustrative embodiment of the present invention, the conductive polymer used to form secondary shield layers 716 and 718 is a polymer that is intrinsically conductive. In an alternative embodiment, secondary shield layers 716 and 718 are comprised of a carrier polymer that is infused with conductive material. The carrier polymer can be substantially any polymer. The filler material can be substantially any conductive material. Examples of filler materials are graphite, carbon fiber and metal powder, such as silver powder.

Coaxial chokes 702 and 704 serve to limit the induced currents in center conductor 706 and primary shield 710. Electrical short 720 couples secondary shield 716 to primary shield 710 at a proximal end of choke 702. Secondary shield 716 terminates at a distal end 730 of choke 702 without electrically coupling to either primary shield 710 or secondary shield 718. Thus, a gap 734 is formed between secondary shield 716 and secondary shield 718. Electrical short 722 couples secondary shield 718 to primary shield 710 at a proximal end of choke 704. Secondary shield 718 terminates at a distal end 732 of choke 704 without electrically coupling to primary shield 710. In an illustrative embodiment, shorts 720 and 722 are formed by soldering the secondary shields 716 and 718 to the primary shield 710.

The dielectric space 712 between primary shield 710 and secondary shield 716 acts as a waveguide that translates short 720 into a high impedance at the open end 730 of choke 702. Similarly, the dielectric space 714 between primary shield 710 and secondary shield 718 acts as a waveguide that translates short 722 into a high impedance at the open end 732 of choke 704. In an illustrative embodiment, the length of each choke 702, 704 (and thus the length of dielectric layers 712, 714 and secondary shields 716, 718) is one-fourth the wavelength of the electromagnetic radiation to be impeded. Thus, in a typical MRI system that employs RF radiation having a wavelength of 300 centimeters (cm), chokes 702 and 704 are designed to have a length of 75 cm. In an illustrative embodiment, the distance between the distal end 730 of choke 702 and short 722 of choke 704 is approximately 1.0 cm.

In an illustrative embodiment of the present invention, intravascular device 700 functions as a guidewire used to assist in the delivery of another intravascular device to an intravascular location. In another illustrative embodiment, device 700 serves as an ablation device adapted to disintegrate intravascular tissue. In such an embodiment, an ablation current is applied to center conductor 706. Distal end 728 of center conductor 706, which heats up as a result of the applied ablation current, is positioned proximate tissue to be ablated.

FIGS. 8a and 8b are schematic diagrams of an intravascular device 800 according to another illustrative embodiment of the present invention. FIG. 8a is a side cross-sectional view of device 800. FIG. 8b is an end cross-sectional view of device 800.

Intravascular device 800 is a coaxial device having two choke mechanisms 802 and 804. Device 800 also includes center conductor 806, dielectric layer 808 and primary shield 810. Choke 802 includes dielectric layer 812, shield 816 and electrical short 820. Choke 804 includes dielectric layer 814, shield 818 and electrical short 822. Shield layers 816 and 818 are electrically conductive.

The proximal end 826 of center conductor 806 extends to and couples to a receiver/controller (not shown). Dielectric layer 812 insulates shield 816 from center conductor 806. Dielectric layer 814 insulates shield 818 from center conductor 806.

In an illustrative embodiment of the present invention, shields 816 and 818 are formed of a conductive polymer in order to reduce the currents induced by RF radiation. In one embodiment, the conductive polymer used to form shield layers 816 and 818 is a polymer that is intrinsically conductive. In an alternative embodiment, shield layers 816 and 818 are comprised of a carrier polymer that is infused with conductive material. The carrier polymer can be substantially any polymer. The filler material can be substantially any conductive material. Examples of filler materials are graphite, carbon fiber and metal powder, such as silver powder, and carbon nanotubes.

Coaxial chokes 802 and 804 serve to limit the induced currents in center conductor 806. Electrical short 820 couples shield 816 to center conductor 806 at a proximal end of choke 802. Shield 816 terminates at a distal end 830 of choke 802 without electrically coupling to either center conductor 806 or shield 818. Thus, a gap 834 is formed between shield 816 and shield 818. Electrical short 822 couples shield 818 to center conductor 806 at a proximal end of choke 804. Shield 818 terminates at a distal end 832 of choke 804 without electrically coupling to center conductor 806. In an illustrative embodiment, shorts 820 and 822 are formed by soldering the shields 816 and 818 to the center conductor 806.

The dielectric space 812 between center conductor 806 and shield 816 acts as a waveguide that translates short 820 into a high impedance at the open end 830 of choke 802. Similarly, the dielectric space 814 between center conductor 806 and shield 818 acts as a waveguide that translates short 822 into a high impedance at the open end 832 of choke 804. In an illustrative embodiment, the length of each choke 802, 804 (and thus the length of dielectric layers 812, 814 and shields 816, 818) is one-fourth the wavelength of the electromagnetic radiation to be impeded. Thus, in a typical MRI system that employs RF radiation having a wavelength of 300 centimeters (cm), chokes 802 and 804 are designed to have a length of 75 cm. In an illustrative embodiment, the distance between the distal end 830 of choke 802 and short 822 of choke 804 is approximately 1.0 cm.

In an illustrative embodiment of the present invention, intravascular device 800 functions as a guidewire used to assist in the delivery of another intravascular device to an intravascular location. In another illustrative embodiment, device 800 serves as an ablation device adapted to disintegrate intravascular tissue. In such an embodiment, an ablation current is applied to center conductor 806. Distal end 828 of center conductor 806, which heats up as a result of the applied ablation current, is positioned proximate tissue to be ablated.

It should be noted that the layers in FIGS. 7a–8b can be electrolytically deposited, chemically deposited, braided on, etc . . . The conductive layers can also be formed of gold, sliver, copper, gold plated copper, or any other such desired material. The antennae associated with these embodiments can be monopole, helical, solenoid or any other desired type of antenna. The center conductor can also be made from stainless steel, Nitinol, copper or copper and gold plated wire, or any other desired conductor, but preferably non-magnetic materials, such as nickel titanium, titanium and tungsten (W).

One problem which presents itself in the present environment is connection of the antenna to the transmission line embodied either simply as a transmission line, as a guidewire, or as a catheter. The conductors associated with the antenna are spaced a very short distance apart and it can be very difficult to form the antennas and connect them to the remainder of the transmission line.

FIGS. 9a–9d illustrate one embodiment for connecting antennas, utilizing a conductive epoxy material. FIG. 9a is a schematic view in which the transmission line formed on a catheter or otherwise as described above is represented as a coaxial transmission line 900 having a shield 902 and a center conductor 904 which are, of course, separated by an insulator or dielectric material. Wire conductors 906 and 908 connect the shield 902 and center conductor 904, respectively, to the exterior of a catheter 910. A solenoid antenna 912 is illustrated and has conductors 914 and 916 connected thereto. In one illustrative embodiment, conductors 914 and 916 are placed closely adjacent the distal end of conductors 906 and 908, and drops of conductive epoxy 918 and 920 are simply disposed across the pairs of conductors to connect them. A variety of electrically conductive epoxies and known, and commercially available, and substantially any of them can be used in accordance with the present invention.

FIG. 9b is an end cross-sectional view taken along section lines 9b–9b. FIG. 9b shows that the conductive epoxy drops 918 and 920 are disposed on opposite radial ends of the catheter 910.

FIGS. 9c and 9d also illustrate a connection between a transmission line 930 and a solenoid antenna 912 utilizing conductive epoxy. However, rather than transmission line 930 being a coaxial transmission line, as shown in FIGS. 9a and 9b, the transmission line is simply formed of flat conductors 932 and 934 which are disposed on an exterior periphery (or an interior periphery, or embedded in the wall of) a catheter 936. Again, the distal ends of conductors 932 and 934 are exposed at the distal end of the catheter and the conductors connected to solenoid antenna 912 are simply placed adjacent the distal end of conductors 932 and 934 and drops of conductive epoxy 918 and 920 are placed thereon.

FIG. 9d is a sectional view taken along section lines 9d–9d and illustrates a somewhat similar arrangement to that shown in FIG. 9b. The conductive epoxy allows a number of advantages. For example, it is softer than conventional solder and thus allows the catheter to bend more easily. This allows the catheter to more easily track vasculature in applications where the device is deployed in tortuous vasculature.

FIGS. 10a and 10b illustrate another embodiment for forming an antenna on the distal end of a catheter. Rather than having a separate wire disposed at the distal end of the catheter, FIG. 10a (which is a cross sectional view of a portion of a catheter) shows an antenna 950 which is coupled to a proximal transmission line 952 represented as a coaxial transmission line (although any other transmission line can be used as well). Antenna 950 is illustratively formed by electroplating conductive portions 954 and 956 on the distal end of a catheter 958. The electroplated sections are illustratively a pair of parallel conductors connected to transmission line 952 and thus become a dipole antenna. While FIGS. 10a and 10b illustrate this type of antenna, substantially any shape can be electroplated on the end of catheter 958 to form substantially any type of antenna, such as a helical antenna, a solenoid antenna, a monopole antenna, etc.

FIG. 10b is an end view taken from the distal end of catheter 958 and similar items are similarly numbered to those shown in FIG. 10a. It should also be noted, of course, that the electroplating need not be formed on a catheter, but may be formed on a guidewire structure.

FIGS. 11a–11c illustrate yet another embodiment for connecting an antenna (or forming an antenna and connecting it) to a proximal transmission line. A wide variety of catheters are braided with material that forms an exterior, an interior, or is integrally formed with the walls of a catheter. In some such catheters, the braid material is an electrically conductive material, such as tungsten, stainless steel, or another ferromagnetic material. FIG. 11a illustrates an enlarged portion of a catheter 970 which includes a catheter wall 972 and a plurality of braided strands 974 and 976. Only two strands are illustrated for the sake of clarity, although it will be appreciated that, in some embodiments, many strands are braided together to form a substantially continuous surface. FIG. 11b illustrates the catheter 970 shown in FIG. 11a, with the catheter wall 972 removed and with braid strand 974 removed. Thus, FIG. 11b better illustrates the shape of braid strand 976, by itself. It will be noted, of course, that the natural conformation of the braided strand 976 is that of a helical antenna. Therefore, in accordance with one embodiment of the present invention, the braid strand, itself, forms a helical antenna. In that embodiment, it is only necessary for the braid strands to be electrically insulated from one another.

FIG. 11c illustrates another embodiment. In the embodiment shown in FIG. 11c, the braid strands form the conductors that are connected to antenna 980 which is disposed at the distal end of the catheter. Since the braid strands are formed of conductive material and already run from a proximal region of the catheter to a distal region, they are already in place and can be conveniently used to form the conductors for connection to the antenna. Of course, in this embodiment, as with the previous embodiment, if the conductors contact one another in the braid, they must be insulated. Utilizing the braid structure avoids the necessity of consuming extra space in the catheter with additional conductors.

It should also be noted, in the embodiment shown in FIGS. 11a–11c that where multiple braids are used, a plurality of braids can be used for each conductor. Similarly, a plurality of braids can be used to form a shield in the transmission line.

FIG. 11d illustrates a plurality of different embodiments of transmission lines. The embodiments illustratively include one catheter or guidewire or a plurality of coaxially arranged catheters or sleeves 982 and 984. The embodiments utilizing only one of the sleeves will be described with respect to sleeve 982, but it should be noted that these embodiments could be utilized if sleeve 982 were a guidewire as well. Sleeve 982 has a plurality of wires or conductors therearound. In the embodiment shown, sleeve 982 has wires a, b, c, and d forming a positive helical braid or counter-wound windings in a positive direction (using the right-hand rule) and wires w, x, y and z form a negative helix or windings in the negative direction. This allows the transmission line to be formed in a variety of different ways.

The following discussion illustrates but a few. The transmission line can be formed using conductors a, b, c, d, in parallel and conductors w, x, y, z in parallel forming twin leads. The transmission can also be formed of a and b (or similar pair) only; a and w (or similar pair) only; a, b and w, x; or a, c, w, y and b, d, x, z, to name but a few examples.

In other embodiments, sleeve 984 is used with windings e, f, g, h oriented similar to, windings a, b, c, d, and with windings s, t, u, v, oriented similar to windings w, x, y, z. The transmission line can then be formed of outer wires a, b, c, d, w, x, y, z and inner wires e, f, g, h, s, t, u, v, concentrically disposed within the outer wires. In yet another embodiment, sleeve 984 (and its associated wires) is axially movable within sleeve 982 (and its associated wires). It should also be noted that sleeve 984 can, instead, be a guidewire. Similarly, when any of the devices described herein are referred to as tubes, sleeves or catheters, they can be guidewires or solid core devices, where suitable (e.g., if nothing needs to travel therethrough). Also, the catheters described herein can be used with guidewires.

In summary, one embodiment of the present invention is directed to an elongated intravascular device (e.g., device 300 or 400) that includes an elongated electrical conductor (e.g., conductor 302 or 402), a first electrically conductive layer (e.g., layer 310, 410 or 422) at least one dielectric layer (e.g., layer 304, 308, 404, 408 or 420), and an electrically conductive coil (e.g., 318 or 412). The first electrically conductive layer is disposed coaxially to the elongated electrical conductor. The dielectric layer is disposed between the elongated electrical conductor and the first electrically conductive layer. A first end of the coil is electrically coupled to the elongated electrical conductor. The second end of the coil is electrically coupled to the first electrically conductive layer. A circuit made up of the elongated electrical conductor, the electrically conductive layer, the dielectric layer and the coil forms an impedance-matching circuit.

Another embodiment of the present invention is directed to an intravascular device 500 that has a cylindrical inner wall 504 and a cylindrical outer wall 502. The cylindrical inner wall 504 defines a lumen 508 and is formed of an expandable electrically conductive material. The cylindrical outer wall 502 is also formed of an expandable electrically conductive material. The inner and outer walls 504, 502 are separated by a compressible dielectric material 506, wherein varying the pressure in the lumen 508 changes the spacing 510 between the inner and outer walls 504, 502, thereby changing the capacitance between the inner and outer walls 504, 502.

Another embodiment of the present invention is directed to an elongated intravascular device 700 that includes an elongated electrical conductor 706, first dielectric layer 708, second dielectric layer 712, 714, primary shield layer 710, secondary shield layer 716, 718, first electrical short 720, second electrical short 722, and a non-electrically-conductive gap 734 in the secondary shield layer 716, 718. The first dielectric layer 708 is disposed on top of the elongated electrical conductor 706. The primary shield layer 712, 714 is electrically conductive and is disposed on top of the first dielectric layer 708. The second dielectric layer 712, 714 is disposed on top of the primary shield layer 710. The secondary shield layer 712, 714 is comprised of an electrically conductive polymer and is disposed on top of the second dielectric layer 712, 714. The first electrical short 720 couples the primary shield layer 710 to the secondary shield layer 716 at a first longitudinal position along the elongated electrical conductor 706. The second electrical short 722 couples the primary shield layer 710 to the secondary shield layer 718 at a second longitudinal position, distal of the first longitudinal position, along the elongated electrical conductor 706. The non-electrically-conductive gap 734 is located in the secondary shield layer 716, 718 at a longitudinal position just proximal of the second electrical short 722.

Another embodiment of the present invention is directed to an elongated intravascular device 800 that includes an elongated electrical conductor 806, a dielectric layer 812, 814, a shield layer 816, 818, first and second electrical shorts 820 and 822, and a non-electrically-conductive gap 834 in the shield layer 816, 818. The dielectric layer 812, 814 is disposed on top of the elongated electrical conductor 806. The shield layer 812, 814 is comprised of an electrically conductive polymer disposed on top of the dielectric layer 812, 814. The first electrical short 820 couples the elongated electrical conductor 806 to the shield layer 816 at a first longitudinal position along the elongated electrical conductor 806. The second electrical short 822 couples the elongated electrical conductor 806 to the shield layer 818 at a second longitudinal position, distal of the first longitudinal position, along the elongated electrical conductor 806. The non-electrically-conductive gap 834 is located in the shield layer 816, 818 at a longitudinal position just proximal of the second electrical short 822.

Still other embodiments of the present invention are directed to connecting an antenna to a transmission line on an intravascular device using conductive epoxy. A number of embodiments of this are set out in FIGS. 9a–9d.

Another embodiment of the present invention is directed to electroplating portions of the antenna on a catheter. One embodiment of this is illustrated in FIGS. 10a and 10b. Still another embodiment of the present invention is directed to using braided fibers, on braided catheters, as either the antenna itself, or as conductors leading to an antenna which is separately connected. Embodiments of this is illustrated in FIGS. 11a–11d.

It is to be understood that even though numerous characteristics and advantages of various embodiments of the present invention have been set forth in the foregoing description, together with details of the structure and function of various embodiments of the invention, this disclosure is illustrative only, and changes may be made in details, especially in matters of structure and arrangement of parts within the principles of the present invention to the full extent indicated by the broad general meaning of the terms in which the appended claims are expressed. For example, the intravascular antennae of the present invention may be employed in intravascular positioning systems that use non-radio frequency communication signals, for example, x-ray signals, without departing from the scope and spirit of the present invention. Other modifications can also be made.

What is claimed is:

1. An elongated intravascular device adapted to be advanced through a vessel of a subject, the device comprising:
   an elongated electrical conductor;
   a first electrically conductive layer disposed coaxially to the elongated electrical conductor;
   at least one dielectric layer disposed between the elongated electrical conductor and the first electrically conductive layer; and
   an electrically conductive coil, a first end of the coil being electrically coupled to the elongated electrical conductor and a second end of the coil being electrically coupled to the first electrically conductive layer, wherein a circuit comprising the elongated electrical conductor, the electrically conductive layer, the dielectric layer and the coil forms an impedance-matching circuit.

2. The intravascular device of claim 1 wherein to electrically conductive coil is an antenna adapted to receive an electromagnetic signal and to transmit the signal to the elongated electrical conductor.

3. The intravascular device of claim 1 wherein the intravascular device is a catheter and wherein the elongated electrical conductor, to first electrically conductive layer, to at least one dielectric layer and the coil are disposed within the catheter shaft.

4. The intravascular device of claim 3 and further comprising:
a guidewire, the catheter being axially movable relative to the guidewire.

5. The intravascular device of claim 1 wherein the intravascular device comprises a guidewire and wherein the elongated electrical conductor, the first electrically conductive layer, and the at least one dielectric layer are disposed on the guidewire.

6. An elongated intravascular device adapted to be advanced through a vessel of a subject, the device comprising:
an elongated electrical conductor;
a first electrically conductive layer disposed coaxially to the elongated electrical conductor;
at least one dielectric layer disposed between the elongated electrical conductor and the first electrically conductive layer;
an electrically conductive coil, a first end of the coil being electrically coupled to the elongated electrical conductor and a second end of the coil being electrically coupled to the first electrically conductive layer, wherein a circuit comprising the elongated electrical conductor, the electrically conductive layer, the dielectric layer and the coil forms an impedance-matching circuit; and
an electrically conductive shield layer disposed coaxially to the elongated electrical conductor, wherein the at least one dielectric layer disposed between the elongated electrical conductor and the coaxial electrically conductive layer comprises a first dielectric layer disposed between the elongated electrical conductor and the shield layer and a second dielectric layer disposed between the shield layer and the first electrically conductive layer.

7. The intravascular device of claim 6 further comprising:
a second electrically conductive layer disposed coaxially to the first electrically conductive layer, the second conductive layer being electrically coupled to the elongated electrical conductor and to the first end of the coil; and
a third dielectric layer disposed between the first electrically conductive layer and the second electrically conductive layer.

8. The intravascular device of claim 7 wherein the first dielectric layer is disposed on top of the elongated electrical conductor, the shield layer is disposed on top of the first dielectric layer, the second dielectric layer is disposed on top of the shield layer, the first electrically conductive layer is disposed on top of the second dielectric layer, the third dielectric layer is disposed on top of the first electrically conductive layer, and the second electrically conductive layer is disposed on top of the third dielectric layer.

9. The intravascular device of claim 6 wherein the coil is wound around a first longitudinal portion of the elongated conductor, the first dielectric layer is disposed on top of a second longitudinal portion of the elongated electrical conductor, the shield layer is disposed on top of the first dielectric layer, the second dielectric layer is disposed on top of the shield layer and the first electrically conductive layer is disposed on top of the second dielectric layer, wherein a third dielectric layer is disposed coaxially on top of a third longitudinal portion of the elongated electrical conductor, the first longitudinal portion of the electrical conductor being longitudinally disposed between the second and third longitudinal portions, and wherein a second electrically conductive shield layer is coaxially disposed on top of the third dielectric layer and electrically coupled to the first electrically conductive layer and to to second end of the coil.

10. An intravascular device comprising:
a cylindrical inner wall defining a lumen and formed of an expandable electrically conductive material; and
a cylindrical outer wall formed of an electrically conductive material, the inner and outer walls separated by a compressible dielectric material, wherein varying the pressure in the lumen changes the spacing between the inner and outer walls, thereby changing the capacitance between the inner and outer wall; and
an electrically conductive coil, a first end of the coil being electrically coupled to a distal end of the inner wall and a second end of the coil being electrically coupled to a distal end of the outer wall, wherein a proximal end of the inner wall and a proximal end of the outer wall are electrically coupled to respective transmission lines, whereby a circuit comprising the coil, the inner wall, the outer wall and the respective transmission lines can be tuned by varying the pressure within the lumen, thereby changing the capacitance between the inner and outer walls.

11. The intravascular device of claim 10 wherein the compressible dielectric material is air.

12. The intravascular device of claim 10 wherein the compressible dielectric material is an air-filled porous material.

13. The intravascular device of claim 10, wherein the compressible dielectric material comprises EPTFE material.

14. The intravascular device of claim 10 wherein the inner and outer walls are comprised of an elastic material coated with an electrically conductive material.

15. The intravascular device of claim 10 wherein the intravascular device comprises a catheter.

16. The intravascular device of claim 15 and further comprising a guidewire, the catheter axially movable relative to the guidewire.

17. The intravascular device of claim 10 wherein the intravascular device comprises a balloon.

18. The intravascular device of claim 10 wherein the outer wall is formed of an expandable material.

19. The intravascular device of claim 10 wherein the outer wall is formed of a substantially rigid material.

20. The intravascular device of claim 10 wherein the intravascular device comprises a guidewire.

21. An elongated intravascular device comprising:
an elongated electrical conductor;
a first dielectric layer disposed on top of the elongated electrical conductor;
an electrically conductive primary shield layer disposed on top of the first dielectric layer;
a second dielectric layer disposed on top of the primary shield layer;

a secondary shield layer comprised of an electrically conductive polymer disposed on top of the second dielectric layer;

a first electrical short coupling the primary shield layer to the secondary shield layer at a first longitudinal position along the elongated electrical conductor;

a second electrical short coupling the primary shield layer to the secondary shield layer at a second longitudinal position, distal of the first longitudinal position, along the elongated electrical conductor, and a non-electrically-conductive gap in the secondary shield layer at a longitudinal position just proximal of the second electrical short.

22. The intravascular device of claim 21 wherein the second dielectric layer includes a longitudinal section, distal of the second electrical short, that serves as a waveguide, and wherein the waveguide translates the second electrical short into a high impedance at a third longitudinal position distal of the second electrical short.

23. The intravascular device of claim 21 wherein a distal end of the elongated electrical conductor is electrically coupled to a distal end of the primary shield layer to form an antenna adapted to receive an electromagnetic signal and to transmit the signal to a controller coupled to a proximal end of the elongated electrical conductor and a proximal end of the primary shield.

24. The intravascular device of claim 23 wherein the elongated intravascular device is adapted to serve as a guidewire adapted to assist in the delivery of a second intravascular device to an intravascular location.

25. The intravascular device of claim 21 further comprising:

an electrically conductive coil having a first end electrically coupled to a distal end of the elongated electrical conductor and a second end electrically coupled to a distal end of the primary shield layer to form an antenna adapted to receive an electromagnetic signal and to transmit the signal to a controller coupled to a proximal end of the elongated electrical conductor and a proximal end of the primary shield.

26. An elongated intravascular device comprising:
an elongated electrical conductor;
a dielectric layer disposed on top of the elongated electrical conductor;
a shield layer comprised of an electrically conductive polymer disposed on top of the dielectric layer;
a first electrical short coupling the elongated electrical conductor to the shield layer at a first longitudinal position along the elongated electrical conductor;
a second electrical short coupling the elongated electrical conductor to the shield layer at a second longitudinal position, distal of the first longitudinal position, along the elongated electrical conductor; and
a non-electrically-conductive gap in the shield layer at a longitudinal position just proximal of the second electrical short.

27. The intravascular device of claim 26 wherein the dielectric layer includes a longitudinal section, distal of the second electrical short, that serves as a waveguide, and wherein the waveguide translates the second electrical short into a high impedance at a third longitudinal position distal of the second electrical short.

28. The intravascular device of claim 26 wherein the elongated intravascular device is a guidewire adapted to assist in the delivery of a second intravascular device to an intravascular location.

29. An intravascular device, comprising:
an elongate catheter having an elongate shaft with a proximal end and a distal end;
an antenna formed of conductive material electroplated on a distal region of the elongate shaft; and
a first elongate conductor and a second elongate conductor, the first and second elongate conductors extending from a proximal region of the elongate member to a distal region thereof and at least one of the first and second elongate conductors being electrically connected to the antenna.

30. The intravascular device of claim 29 wherein the antenna comprises:
a plurality of portions of conductive material electroplated on a distal region of the elongate shaft and in spaced relation to one another about the elongate shaft.

31. The intravascular device of claim 30 wherein each of the portions of conductive material are electrically connected to one of the first and second elongate conductors.

* * * * *